United States Patent [19]
Sefton

[11] 4,209,014
[45] Jun. 24, 1980

[54] DISPENSING DEVICE FOR MEDICAMENTS
[75] Inventor: Michael V. Sefton, Toronto, Canada
[73] Assignee: Canadian Patents and Development Limited, Ottawa, Canada
[21] Appl. No.: 859,314
[22] Filed: Dec. 12, 1977
[51] Int. Cl.$^2$ ............................................. A61M 5/00
[52] U.S. Cl. ................... 128/214 F; 128/215; 128/220; 128/234; 128/260; 128/DIG. 1
[58] Field of Search ................. 128/1.3, 213, 214 F, 128/218 A, 220, DIG. 1, 260, 2 R, 214 E, DIG. 13, 234, 235, 236, 237, 238, 261, 269, 215; 401/171, 176, 179, 143

[56] References Cited
U.S. PATENT DOCUMENTS

| | | | |
|---|---|---|---|
| 1,213,655 | 1/1917 | Keil | 401/179 |
| 1,410,530 | 3/1922 | Larche' | 128/220 |
| 1,578,517 | 3/1926 | Hein | 128/220 |
| 1,860,277 | 5/1932 | Dennis | 401/143 |
| 2,605,765 | 8/1952 | Kollsman | 128/214 F |
| 3,512,940 | 5/1970 | Shapiro | 128/220 X |
| 3,604,417 | 9/1971 | Stolzenberg | 128/260 X |
| 3,850,348 | 11/1974 | Bessot | 128/214 F |
| 3,975,350 | 8/1976 | Hudgin | 128/260 X |
| 3,991,750 | 11/1976 | Vickery | 128/260 |
| 4,003,379 | 1/1977 | Ellinwood | 128/260 |
| 4,055,175 | 10/1977 | Clemens et al. | 128/213 |
| 4,103,686 | 8/1978 | LeFevre | 128/274 X |

*Primary Examiner*—Paul T. Sewell
*Assistant Examiner*—James R. Feyrer
*Attorney, Agent, or Firm*—Ronald G. Bitner

[57] ABSTRACT

An implantable device for dispensing a medicament in two modes; a basal delivery rate and an augmented rate. The device includes a permeable elastic material adapted to be repeatedly compressed by a solenoid operated piston. The device delivers a basal rate when the piston is inoperative and an augmented rate when the permeable elastic material is compressed. The device is suitable for delivering insulin in an "artificial endocrine pancreas".

2 Claims, 4 Drawing Figures

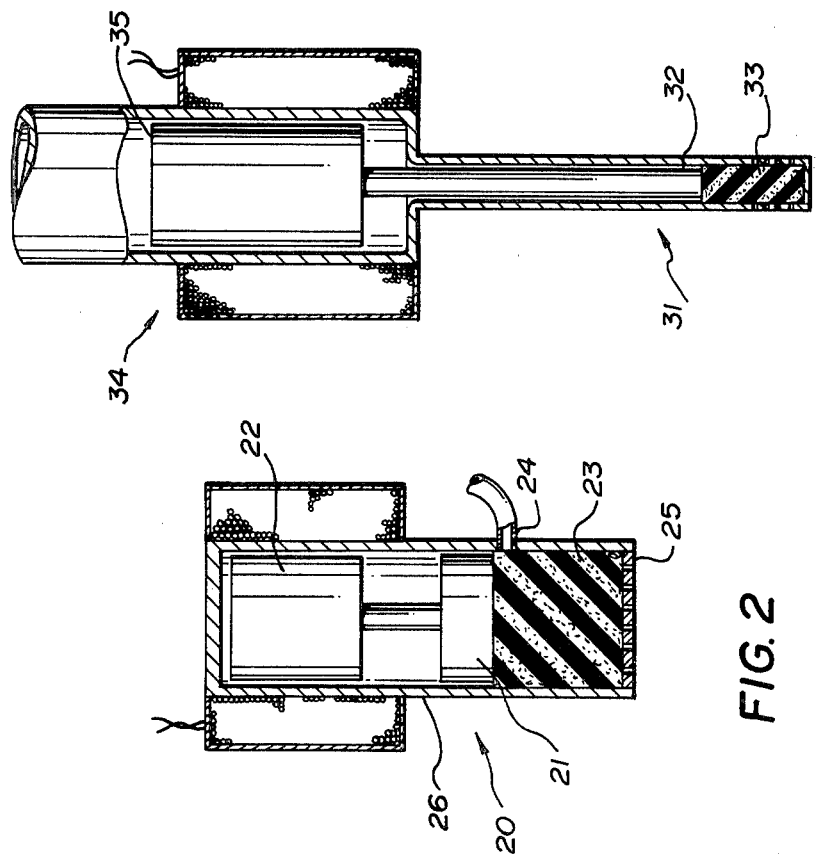
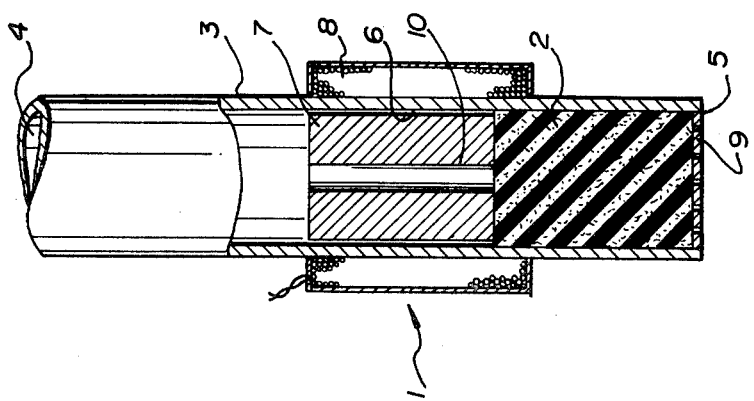

DISPENSING DEVICE FOR MEDICAMENTS

BACKGROUND OF THE INVENTION

This invention relates to a device for dispensing medicaments.

Conventional administration of drugs takes two general forms—periodic injection or ingestion, or continuous infusion. Periodic administration has the disadvantage that the drug level within the body varies from above optimum initially and falls below optimum, resulting in poor maintenance of the patient and inefficient use of the drug. Increasing the number of applications minimizes the adverse effects of high dosages and improves efficiency but results in higher costs and more inconvenience to the patient. Infusion therapy can provide a relatively constant dose level but is limited by the bulky nature of the medicament preparation and by the expert care needed for safe administration.

In recent years, polymeric membranes have been used to encapsulate medicament preparations to slow and control the release of the active substance, allowing the body to be maintained at the optimum level over a relatively long time. Controlled release formulations have two deficiencies which limit their use—the amount of drug that can be encapsulated and implanted is relatively small, and it is not possible to vary the rate of release of the drug. The inability to vary the release rate limits the use to those agents which have a constant demand rate or a constant clearance rate, and is not entirely satisfactory for insulin therapy.

Insulin is required by the body in varying amounts with a greater amount being required during and immediately after a meal when the glucose level rises. The controlled release formulation while maintaining a basal amount of insulin in the blood, cannot increase the amount of insulin to counteract the increased glucose level after a meal.

It has been proposed, for example, in U.S. Pat. No. 3,923,060 to E. H. Ellinwood, Jr., to provide an implantable apparatus for dispensing medications within the body over a long period of time in accordance with the needs of the patient by providing sensors which monitor a particular body condition and powered dispensing means responsive to the sensed data. The aforesaid patent also describes a device specifically for dispensing insulin, having two dispensing elements, one to dispense a daily average dose on a regular basis and one to dispense intermittently when the need arises. The device described requires that each dispensing element is provided with a separate pump, pump driving means and associated logic circuit. This arrangement requires two separate dispensing units and associated energizing means, and in the event of an interruption of energy, no medication would be dispensed.

SUMMARY OF THE INVENTION

It has been found that a relatively simple medicament dispensing device can be provided with the use of a permeable elastic material in which delivery of the medicament can be increased by repeated compression of the permeable elastic material to provide a controllable delivery rate.

It has also been found that repeated compression of the permeable material can increase delivery without the use of check valves for preventing back flow. Although the reason for this is not understood with certainty, it is believed that as the piston compresses the elastic permeable material, the portion of the material in contact with and near the piston surface is compressed to a degree that it is rendered relatively impermeable in comparison with the material at the opposite outlet end, and thereby reduces backflow while allowing flow in the direction of the outlet.

The present invention provides a device for dispensing a medicament comprising: an elastic material permeable to the medicament; a housing for confining the elastic material, said housing having an inlet for connection with a supply of the medicament, and an outlet for delivery; a reciprocatable piston for repeatedly compressing the elastic material, and means for activating said piston; the device being operative to deliver a basal rate of the medicament when the piston is inoperative, and an augmented rate when the elastic material is compressed.

The present invention is well suited for delivering a highly concentrated medicament preparation thereby facilitating the design and use of an implanted device.

BRIEF DESCRIPTION OF THE DRAWINGS

FIG. 1 is a partly sectional view of a device for dispensing a medicament in accordance with the present invention.

FIGS. 2 and 3 are partly sectional views of alternative embodiments of a dispensing device.

DESCRIPTION OF THE PREFERRED EMBODIMENTS

Figure 4:
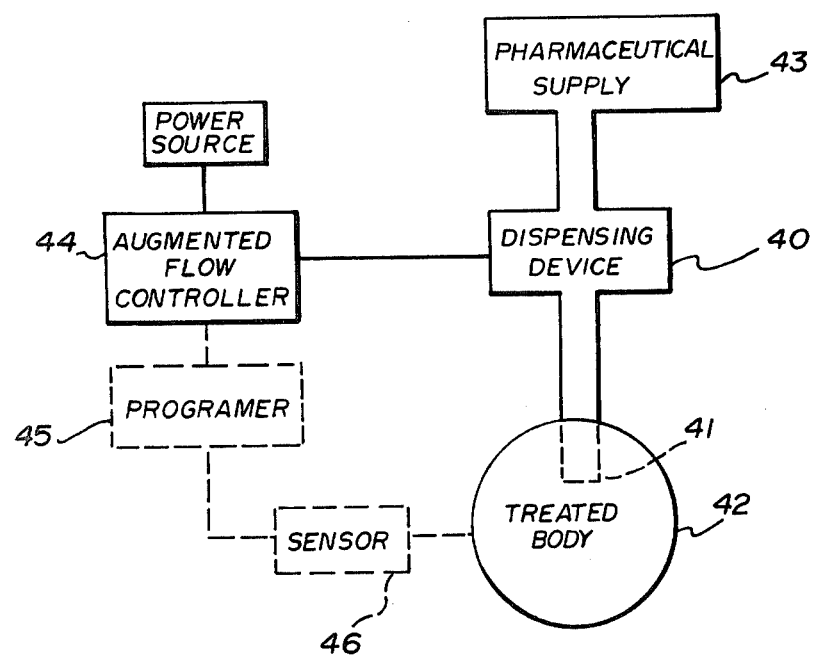
FIG. 4 is a schematic illustration of a system incorporating the dispensing device of the present invention.

Referring to FIG. 1, the medicament dispensing device 1 includes an elastic material 2 that is permeable to the medicament. The permeable elastic material 2 is contained by a suitable housing 3 having an inlet 4, for connecting with a supply of the medicament, and an outlet 5. Reciprocatably disposed within a cylindrical portion 6 of the housing 3 is a piston 7 for compressing the elastic permeable material 2. The piston 7 is made of a magnetic material and compression of the elastic material 2 is effected by means of a solenoid coil 8. The permeable material 2 is confined at the outlet by a suitable porous or apertured plug 9. Means, in the form of a passageway 10, is provided for allowing the medicament to bypass the piston 7 to the permeable material 2.

In operation, with the inlet 4 connected to a suitable supply of a medicament, the concentration difference and/or the pressure difference across the permeable elastic material 2 results in diffusion or bulk transport through the material 2. The medicament flows through the passageway 10, and also around the outside of the piston if sufficient clearance is provided, and exits at outlet 5. Hereinafter, the flow that takes place while the solenoid-piston is inactive is referred to as basal delivery. The basal rate for a particular medicament is a function of the concentration and/or pressure difference across the permeable elastic material, and the permeability of the material.

Augmented delivery is achieved by repeated compression and decompression of the material 2 by means of the piston 7. Compression is effected by the magnetic piston 7 when current is applied to the solenoid coil and decompression occurs when current supply is interrupted. The augmented delivery rate is a function of the permeability and mechanical properties, such as the modulus of elasticity, of the material, and also on the solenoid design. For a given device the augmented delivery rate is a function of the frequency of compression and the displacement of the material with each cycle of compression. The displacement can be varied by varying the current through the solenoid coil.

FIG. 2 illustrates another embodiment of the present invention. The device 20 is basically similar to that of FIG. 1, and has a piston 21 connected to solenoid core 22 for compressing the permeable elastic material 23, an inlet 24 and outlet 25 within a housing 26.

For basal delivery, the piston 23 is in the upper position, as shown, and the medicament enters at inlet 24, diffuses through the material 23 and exits at outlet 25. The inlet 24 is positioned in the housing 26 so as to be alternately blocked and unblocked by the piston 21 in the augmented delivery mode. As the piston 21 travels downward, it blocks the inlet 24 reducing backflow as the material 23 is compressed and thereby increasing efficiency.

FIG. 3 shows another embodiment of the invention in which the outlet portion 31 of the device, including the piston 32 and permeable elastic material 33, has a cross-sectional size smaller than that of the inlet portion 34 including the solenoid core 35. This embodiment is particularly suitable for the administration of a medicament directly into a small vessel.

Preferably the permeable elastic material will have a tensile modulus of elasticity of not greater than $10^4$ psi in order to minimize power consumption. Examples of suitable materials include: polyvinyl alcohol hydrogels, polyhydroxyethyl methacrylate hydrogels, polyacrylamide gels, agarose gels, gels made from polyelectrolytes, acrylic polymers, vinyl pyridine, vinyl pyrrolidone, cellulose and cellulose derivatives, or polyurethane and other polymeric foams.

FIG. 4 illustrates schematically a complete system for administering a medicament, which could, for example, be insulin to treat diabetes mellitus. In this system the dispensing device 40, which may be of the type illustrated in FIGS. 1, 2 or 3, has its outlet 41 positioned in the body to be treated. Alternatively the entire dispensing device may be implanted in the body 42. The dispensing device 40 is supplied with a medicament from a suitable reservoir 43 which may also be implanted in the body.

In operation, a basal rate of a medicament, such as insulin for example, is delivered while the solenoid-piston is inoperative. When increased insulin delivery is required, such as during and after meals, the solenoid-piston is activated by control means 44 which provides a periodic pulse of current of selected magnitude and frequency to provide the desired augmented flow. The controller 44 may be activated manually or by a suitable programer 45. The programer 45 may, for example, provide for progressively decreasing delivery of insulin from the beginning of a meal to a predetermined time later. Alternatively, or in addition, the glucose concentration may be monitored by a suitable sensor 46 to control the amount of insulin delivered.

In addition to treating diabetes mellitus, the present invention may be used for various other conditions where variable delivery rate is required, such as cardiac function control or cancer chemotherapy.

EXAMPLE

A 7 mm outside diameter glass tube was capped at one end with a sintered glass disc. A 3 mm thick cylindrical section of flexible polyurethane foam (HYPOL ®, W. R. Grace & Co.) made from 100 parts FHP 3000, 70 parts water, and 1.0 part L520 (Union Carbide) was forced into the tube. A 2.5 cm long mild steel rod (4.8 mm diameter) with a 1.4 mm diameter central bore was used as piston. Two thousand turns of number 36 enamelled copper wire was wrapped about the outside of the tube, so that there was a 2 mm offset between the end of the coil and the end of the piston. A piece of transformer iron was then wrapped about the coil to make an external field path.

A feed solution consisting of 143 ppm amaranth (a tracer molecule) and 0.35 units/ml of insulin in phosphate buffered saline (pH 7.4) was prepared within a sterile infusion bottle. The concentration of amaranth was determined by quantitative ultraviolet spectroscopy, at a wavelength of 220 nm, comparing the absorption of a test solution with the absorption of a set of standards. The addition of a small quantity of insulin labelled with radioactive iodine ($I^{125}$), enabled changes in the concentration of insulin to be determined. The activity of an insulin solution measured in a gamma counter was compared with that of the feed solution.

The remainder of the glass tube was filled with the solution as was a tube connecting with the inverted feed bottle. The outlet end of the glass tube was placed in 100 ml of well stirred saline, the level of which was maintained a constant amount (17 cm) below the level of the feed solution.

Characterization of the device consisted of following the amaranth concentration and insulin activity in the product receiver as a function of time in the absence of any current through the coil (basal delivery) and in the presence of such a current (augmented delivery).

For the particular device described above, the basal delivery rate of amaranth was 18.5 micrograms per minute or 0.027 grams/day and the basal delivery rate of insulin was $5.5 \times 10^{-2}$ units/minute or 79 units/day. With a current of 620 mA passing through the coil (60 volts), and the foam compressed 26 times per minute, the delivery rate of amaranth was increased to 54.5 micrograms per minute. The delivery rate of insulin was increased under these conditions to 0.17 units/minute. The amaranth delivery rate was augmented by a factor of 2.95 and the insulin delivery rate was augmented by a factor of 3.06. Since the power is on for about 0.1 seconds per cycle, the average power utilization is approximately 1.7 watts for augmented delivery and no power consumption for basal delivery.

Additional experiments, under different conditions, indicate that augmentation factors higher than those given above are obtainable. For example, a shorter offset of the piston with respect to the solenoid coil produced larger forces and higher augmented delivery. It was also found that higher degrees of augmentation are obtained by lowering supply pressure. However, it appears desirable to maintain a small positive pressure across the permeable elastic material.

I claim:

1. A device for dispensing a medicament comprising:
   an elastic material permeable to the medicament;
   a housing for confining the permeable elastic material, said housing having an inlet for connection with a continuous supply of the medicament, and an outlet for delivery;
   a reciprocatable piston for repeatedly compressing the permeable elastic material; and
   means for reciprocating said piston;

the device being operative with a supply of medicament connected to said inlet to deliver the medicament at a basal rate when the piston is inoperative, and at an augmented rate when the permeable elastic material is repeatedly compressed.

2. The device of claim 1 wherein the means for activating the piston comprises a solenoid operatively connected to the piston.

* * * * *